US006982563B2

(12) United States Patent
Hands

(10) Patent No.: US 6,982,563 B2
(45) Date of Patent: Jan. 3, 2006

(54) MONITORING OF CORROSION INDUCED LOSS OF MATERIAL BY MEANS OF A PLURALITY OF ELECTRICAL RESISTANCE MEASUREMENTS (FIELD SIGNATURE METHOD, ELECTRICAL RESISTANCE TOMOGRAPHY)

(75) Inventor: Brian Hands, Cumbria (GB)

(73) Assignee: British Nuclear Fuels PLC, Seascale (GB)

(\*) Notice: Subject to any disclaimer, the term of this patent is extended or adjusted under 35 U.S.C. 154(b) by 0 days.

(21) Appl. No.: 10/416,423

(22) PCT Filed: Nov. 6, 2001

(86) PCT No.: PCT/GB01/04889

§ 371 (c)(1),
(2), (4) Date: Sep. 2, 2003

(87) PCT Pub. No.: WO02/39102

PCT Pub. Date: May 16, 2002

(65) Prior Publication Data

US 2004/0061510 A1 Apr. 1, 2004

(30) Foreign Application Priority Data

Nov. 9, 2000 (GB) .................................. 0027398
Nov. 11, 2000 (GB) .................................. 0027638

(51) Int. Cl.
*G01R 27/08* (2006.01)
*G01N 17/00* (2006.01)
(52) U.S. Cl. .................. 324/700; 324/71.1; 422/53
(58) Field of Classification Search .............. 324/700, 324/71.1, 71.2, 691; 422/53
See application file for complete search history.

(56) References Cited

U.S. PATENT DOCUMENTS

| 1,895,643 | A | 1/1933 | Putnam |
| 3,853,730 | A | 12/1974 | Anderson |
| 4,019,133 | A | 4/1977 | Manley et al. |

(Continued)

FOREIGN PATENT DOCUMENTS

EP 0 150 552 A1 8/1985

(Continued)

OTHER PUBLICATIONS

R. Strommen et al., *The FSM Technology—Operational Experience and Improvements in Local Corrosion Analysis,* Corrosion 96 the NACE International Annual Conference and Exposition, 'Online', No. 338, Mar. 24-29, 1996, pp. 1-15, XP002187991.

(Continued)

*Primary Examiner*—Anjan Deb
*Assistant Examiner*—Timothy J. Dole
(74) *Attorney, Agent, or Firm*—Workman Nydegger

(57) ABSTRACT

A method of monitoring or predicting corrosion using a field signature method is provided which is intended to be applicable to non-linear locations, such as bends, junctions and the like. The method includes obtaining information on a relationship which links voltage measurements, obtained for a location, between two or more electrical contacts in contact with the location at a first time and one or more other times when a current is passed through the location, to the loss of material from the location. The information on the relationship is used in a modelling process which includes the generation of a model of the location, two or more points on that location and modelling the values generated for the voltages which will be measured between the two or more points with a current applied to the location at a first and at least at a second time.

18 Claims, 7 Drawing Sheets

U.S. PATENT DOCUMENTS

| | | | |
|---|---|---|---|
| 4,087,749 A | 5/1978 | McCormack | |
| 4,096,437 A | 6/1978 | Kitzinger et al. | |
| 4,328,462 A | 5/1982 | Jensen | |
| 4,338,097 A | 7/1982 | Turner et al. | |
| 4,338,563 A | 7/1982 | Rhoades et al. | |
| 4,419,892 A | 12/1983 | Goolsby et al. | |
| 4,591,792 A | 5/1986 | Birchmeier et al. | |
| 4,642,557 A | 2/1987 | Ross | |
| 4,703,253 A | 10/1987 | Strommen | |
| 4,814,705 A | 3/1989 | Saunderson | |
| 4,821,204 A | 4/1989 | Hüschelrath | |
| 4,982,154 A | 1/1991 | Schwabe et al. | |
| 5,126,654 A | 6/1992 | Murphy et al. | |
| 5,165,794 A | 11/1992 | Ortiz | |
| 5,171,517 A | 12/1992 | Solomon et al. | |
| 5,217,304 A | 6/1993 | Ortiz | |
| 5,404,104 A | 4/1995 | Rivola et al. | |
| 5,481,198 A | 1/1996 | Patel | |
| 5,486,767 A | 1/1996 | Schwabe et al. | |
| 5,581,037 A | 12/1996 | Kwun et al. | |
| 5,814,982 A | 9/1998 | Thompson et al. | |
| 5,888,374 A | 3/1999 | Pope et al. | |
| 6,077,418 A | 6/2000 | Iseri et al. | |
| 6,680,619 B1 | 1/2004 | Horn | |

FOREIGN PATENT DOCUMENTS

| | | |
|---|---|---|
| EP | 0 224 230 A3 | 6/1987 |
| EP | 0 344 576 A2 | 12/1989 |
| GB | 365 555 | 1/1932 |
| WO | WO 83/03675 | 10/1983 |
| WO | WO 90/04779 | 5/1990 |
| WO | WO 94/09354 | 4/1994 |
| WO | WO 01/69223 A2 | 9/2001 |
| WO | WO 01/70003 A2 | 9/2001 |

OTHER PUBLICATIONS

A. Daaland, *Modeling of Local Corrosion Attacks on a Plate Geometry for Developing the FSM Technology*, Insight, vol. 38, No. 12, Dec. 1996, pp. 872-875.

Roe D. Strommen, et al., *FSM-A Unique Method for Monitoring Corrosion of Steel Piping and Vessels*, Material Performance, vol. 32, No. 3, Mar. 1993, pp. 50-55.

R. Johnson, et al., *Weld Root Corrosion Monitoring with a New Electrical Field Signature Mapping Inspection Tool*, Corrosion 2000, 'Online', Mar. 26-31, 2000, XP002187993.

Roe D. Strommen, et al., *New Technique Monitors Pipeline Corrosion, Cracking, Oil* and Gas Journal, vol. 91, No. 52, Dec. 27, 1993, pp. 88-92.

M. Wang et al., *Modelling and Mapping Electrical Resistance Changes Due to Hearth Erosion in a 'Cold 'Model of a Blast Furnace*, 1$^{st}$ World Congress on Industrial Tomography, Apr. 14-17, 1999, pp. 161-166, XP002187994.

Roe Strommen et al., *FSM (Field Signature Method)—The New Technology for Internal Corrosion Monitoring of Pipelines, Vessels and Pressure Equipment* Proceedings of the 1998 ASME Energy Sources Technology Conference, Houston Texas, Feb. 2-4, 1998, XP00105536.

Initial wall thickness all segments

Final wall thickness middle segments

MONITORING OF CORROSION INDUCED LOSS OF MATERIAL BY MEANS OF A PLURALITY OF ELECTRICAL RESISTANCE MEASUREMENTS (FIELD SIGNATURE METHOD, ELECTRICAL RESISTANCE TOMOGRAPHY)

BACKGROUND OF THE INVENTION

1. Field of the Invention

This invention concerns improvements in and relating to monitoring of loss of material, particularly, but not exclusively, in relation to monitoring erosion through the use of field signature method based investigations and model based predictions of factors involved in such investigations.

2. Relevant Technology

The field signature method is based upon feeding a direct current through a location and measuring the electric field which is generated as a result using an array of electrical contacts on a surface of the location. Changes in the magnitude and shape of the electric field over time can provide significant information on corrosion occurring at the location.

Whilst variations in the voltage between one or more pairs of contacts over time are fairly well understood for linear pipelines and the like, the physical circumstances represented by variations in the voltage for one or more pairs of contacts in other configurations of the location under investigation are far less understood.

SUMMARY OF THE INVENTION

The present invention aims to provide for wider applicability of field signature based techniques by obtaining information about one or more of the factors involved in the characterisation of erosion from measured results, using models to derive those characteristics. The present invention aims to provide for wider applicability of field signature based techniques to measurements of erosion in a variety of non-linear locations, such as beads, junctions and the like.

According to a first aspect of the invention we provide a method of obtaining information on a relationship which link voltage measurements, obtained for a location, between two or more electrical contacts in contact with the location at a first time and one or more other times when a current is passed through the location, to the loss of material from the location, the information on the relationship being obtained by a modelling process, the modelling process including generating a model of the location, the model including two or more points on that location, modelling the values generated for the voltages which would be measured between the two or more points with a current applied to the location at a first time and at least at a second time, the model including a change in configuration of the location between the first time and the second time to model loss of material from the location, the relationship being an expression of the relationship between a factor related to the model voltage values and a factor related to the change in configuration of the model location.

Preferably the information on the relationship is used in a method of investigating material loss from an actual location, but the information on the relationship may be used to build up a database of computer models.

In relation to the actual location being considered, preferably voltage measurements using two or more electrical contacts in contact with the location are made. Preferably the voltage between two or more electrical contacts at a first time and at one or more other times is measured. A current is preferably passed through the location at the time of the voltage measurements. The voltage measurements obtained preferably provide information on the loss of material from the location with time. Preferably an expression of the actual loss of material is obtained using the relationship and the voltage measurements.

Further options, possibilities and features for the first aspect of the invention are set out below.

According to a second aspect of the invention we provide a method of investigating loss of material from a location, the method including:

defining the location and providing two or more electrical contacts in contact with the location;

measuring the voltage between two or more electrical contacts at a first time and at one or more other times, a current being passed through the location at the time of the voltage measurements, the voltage measurements providing information on the loss of material from the location with time, the information on material loss being obtained using a relationships which links the voltage measurements to the loss of material, information on the relationship being obtained by a modelling process, the modelling process including generating a model of the location, the model including two or more points on that location, modelling the values generated values for the voltages which would be measured between the two or more points with a current applied to the location at a first time and at least at a second time, the model including a change in configuration of the location between the first time and the second time to model loss of material from the location, the relationship being an expression of the relationship between a factor related to the model voltage values and a factor related to the change in configuration of the model location.

The first and/or second aspect of the invention may include any of the following features, options or possibilities.

The loss of material may be due to corrosion and/or erosion and/or chemical attack of the location. The loss may be evenly distributed about the location. The loss may be unevenly distributed about the location, for instance greater loss may occur on the outside of pipe bends compared with the inside and/or greater loss may occur where there is pitting or other such loss. No material loss has preferably occurred at the time of the first measurement of the location.

The location is preferably an actual location potentially subjected to material loss. The loss may arise due to the environment with which the location is contacted. Only a part of the location, for instance the inside, may be contacted with the loss causing environment. In particular the location may be a non-linear piece of a pipeline, for instance a curve and/or bend and/or junction between two or more pipelines. In particular the location may be a linear and/or non-linear piece for which localised material loss is anticipated, for instance due to pitting, cracks or the like.

Preferably all the electrical contacts are provided on a single mounting unit. Preferably the separation of two or more, ideally all, of the electrical contacts is fixed in one or more directions. The separation may be fixed in all directions, optionally apart from potential movement into or out of the mounting unit. The electrical contacts may be moveable, for instance being spring loaded, perpendicular to the surface of the mounting unit. The electrical contacts may be provided in a permanent position, for instance by welding.

The electrical contacts may be provided by pins or other electrically conducting elements. Preferably the electrical contacts are resiliently forced into contact with the location, for instance by springs. The electrical contacts may be provided in pairs, preferably with the voltage between predefined pairs being measured during the investigation. The electrical contacts and/or pairs of electrical contacts may be evenly spaced along the direction of current flow and/or unevenly spaced along the direction of current flow. Electrical contacts may be provided throughout the location, in the direction of current flow and/or perpendicular to the direction of current flow. The electrical contacts may be provided all around the cross-section of the location. The method may involve measuring the voltage for one or more pairs of electrical contacts simultaneously. Four or more and preferably eight or more pairs may be considered simultaneously. The number of pins provided may be between 8 and 256 pins, more preferably between 16 and 128 pins and ideally between 24 and 64 pins.

The electrical contacts may be provided by a mounting unit. The mounting unit is preferably provided with one or more surfaces configured to match one or more surfaces of the location to be investigated, ideally to match at least one internal surface of the location. Preferably the electrical contacts are provided on or associated with the one or more matching surfaces. Preferably the electrical contacts project outward from the mounting unit.

The mounting unit may be clamped or otherwise releasably fixed in position once introduced to the location. The mounting unit may be provided in a permanent position once introduced to the location, for instance by welding.

The voltage measured may increase in voltage as corrosion progresses. The variation in voltage with time may occur evenly for all the respective electrical contacts considered. The variation in voltage with time may occur unevenly for all the respective electrical contacts considered. The variation may occur at an even rate over time. The variation may occur at an uneven rate over time.

The voltage measurements may be made after the current has started. Preferably the voltage measurements are made at least 200 $ms^{-1}$ after the current has been applied. Preferably the voltage measurement is made within 800 $ms^{-1}$ of the current being applied. Preferably the voltage measurements are made after the current stops preferentially flowing in the surface part of the sample. Preferably the voltage is steady when the voltage measurements are made.

Preferably the temperature of the two or more electrical contacts is measured at one or more of the first time and one or more other times. Preferably the temperature is measured each time a voltage is measured. The temperature of the two or more electrical contacts may be measured by measuring the temperature of the electrical contacts. The temperature of the two or more electrical contacts may be measured by measuring the temperature of the location. The temperature of the two or more electrical contacts may be measured by measuring the temperature of the environment surrounding the two or more electrical contacts.

Preferably the voltage measurements are compensated for temperature variations at the electrical contacts and/or location and/or reference location and/or the environments thereof.

The voltage measurement at the first time may define a baseline voltage or voltages against which corrosion is considered and/or define a thickness of material forming the location or one or more parts thereof and/or define the shape of the electric field against which variations can be considered.

Preferably the first time is before the one or more other times. The one or more other times may be at regular intervals relative to the first time.

Preferably the method includes providing a power source external of the location to provide an applied current. The power source may be a mains power source or portable power source, such as a battery. The power source may provide the same or a different current level for respective measurements.

The current is preferably a DC current and particularly a square wave DC current. The DC current may be provided in a single direction but is more preferably applied in both directions, ideally alternately. The current may be applied for between 200 and 2000 $ms^{-1}$ per time and more preferably between 500 and 1000 $ms^{-1}$.

The current may be introduced to the location towards one end thereof and leave towards the other end thereof. The current may be introduced and/or exit by a current contact unit. Preferably the current contact unit and/or electrical contacts are configured to match one or more surfaces of the sample. The current contact unit or units may be provided in permanent contact with the location, for instance by welding.

The voltage measurements for the sample may indicate a general level of loss from the location, preferable through consistent variation between the various electrical contact voltages measured for the location and the baseline obtained. The voltage measurements for the location may indicate specific corrosion from parts of the location, preferably through inconsistent variation between the electrical contact voltages at one or more parts of the location and the baseline and the variation between electrical contact voltages at one or more other parts of the location and the baseline.

The information on material loss may be a maximum thickness of loss and/or mass of lost material and/or rate of loss.

Preferably the modelling process is a computer modelling process. The modelling process may generate a three dimensional model of the location. The model may generate the model of the location using a plurality of nodes. Preferably at least 50 such nodes are used to model the geometry of the location, but the number may extend to 10,000 or even more. Preferably the modelling process includes information on the electrical resistance of the material and/or materials forming the location. Preferably the modelling process includes information on the configuration and/or cross sectional profile and/or thickness of the material or materials forming the location.

Preferably a node is provided in the model for each pin in the actual measurement apparatus. Preferably the nodes have corresponding position and/or separation relative to the pins they represent.

Preferably the modelling process includes applying a model electric current to the model location and calculating the induced voltage at two or more of the nodes and ideally at all of the nodes forming the model of the location. Preferably the modeling process includes the extraction of model voltages for the nodes corresponding to the pin positions in the actual apparatus. Preferably the modelling includes a calculation of voltage differences between node pairs. Preferably the modelling process includes calculating such voltages and/or voltage differences at the first time, ideally with no material loss, and at one or more other times with material loss. Preferably at least ten times are calculated using the model. The modelling process may include a comparison of the signal from all known pairs and/or all pins pairs.

The model may simulate material loss by reducing the number of nodes used to simulate the location and/or by moving one or more of the nodes simulating the location.

The modeling process preferably includes the generation of a model of one or more locations. One or more location types may be modelled, for instance, curves, angle bends, junctions. One or more different sizes of locations may be modelled, potentially for the different types as well. One or more different materials may form the location within a model and/or between different models. The model location may be a size and/or configuration and/or material match to an actual location of interest for investigation.

The model may include points which are equated to electrical contacts and/or are the points at which voltage measurements are considered or generated by the model. The points may correspond to the position of electrical contacts in actual measurements.

The current applied in the modelling may correspond to the current level and/or other characteristics applied in actual measurements.

The first and/or second time of measurement consideration in the model may correspond to the first time and/or one or more of the other times of a measurement process.

The change in the configuration of the model location may involve a reduction in thickness of one or more parts of the location. The thickness of the model location may be reduced in thickness evenly along the length of the location and/or perpendicular to the length. The thickness of the model may be reduced in thickness unevenly. The thickness may be reduced preferentially in one or more parts of the location were preferential material loss is anticipated. A phased increase in the extent of material loss may be provided between those parts of the location where no preferential loss is anticipated and those locations were the anticipated preferential loss is greatest. The change in configuration may be achieved by decreasing the exterior extent of the location. The change in configuration may be achieved by increasing the interior extent of a void. For instance, one or more dimensions of an opening with a location, for instance a pipeline, may be increased.

It is particularly preferred for locations with a circular cross-sectioned interior opening to increase the diameter of the opening. The centre of the opening may be kept in the same position, for instance to provide even material loss. The centre of the opening may be moved in one direction, for instance to provide preferential material loss from the part of the location in that direction. The level of increase may vary along the location's extent, for instance by increasing the dimension to different extents.

The method may include a comparison of the voltage differences, or more preferably a fingerprint coefficient, for one or more nodes/pin pairs arising from the modelling process with a simulation of metal loss against the voltage differences, or more preferably a fingerprint coefficient, arising for one or more pin pairs in the actual location. The method may include the adoption of a simulation of material loss to equate to the material loss from the actual location if the comparison is acceptable and/or the consideration of an alternative model based on an alternative simulation of the material loss if the comparison is not acceptable. The acceptability of the comparison may be based on a statistical analysis and/or fitting process.

The method may include the generation of a plurality of models based on different simulations of material loss and the consideration of which these models best represents the actual corrosion occurring, ideally due to the correspondence of the model voltage differences and the actual location voltage differences.

The relationship may provide an expression of the corrosion as a thickness loss, proportion of material lost or other value, such as a rate of loss. The corrosion may be expressed in terms of the change between the as new state represented by the first time measurements and the corroded state of one or more of the other time measurements and/or in terms of the progress of corrosion from the first time onwards.

The relationship may be a linear relationship between the factors. The relationship may extent from the X-Y intersection of a plot of the relationship.

The factor relating to the model voltage values may be a fingerprint coefficient and more particularly the maximum fingerprint coefficient measured for that configuration variation. The fingerprint coefficient may be expressed in ppt (parts per thousand).

The facture relating to the change in configuration for the model location may be a level of material loss, more particularly the maximum material loss. The maximum material loss may be expressed in microns.

The relationship is preferably used to provide information on the material loss in the measured location, and in particular by equating a measured factor relating to the measured voltage to a material loss. More particularly the measured voltage factor may be a fingerprint coefficient, ideally the maximum fingerprint coefficient for that measurement time. The material loss of the measured location is preferably expressed as a thickness of material loss, ideally as a maximum thickness of material loss.

The modelling of the configuration change may include both changes to reflect even loss of material and preferential loss of material.

BRIEF DESCRIPTION OF THE DRAWINGS

Various embodiments of the invention will now be described, by way of example only, and with reference to the accompanying drawings in which.

DETAILED DESCRIPTION OF THE PREFERRED EMBODIMENTS

Figure 1A:
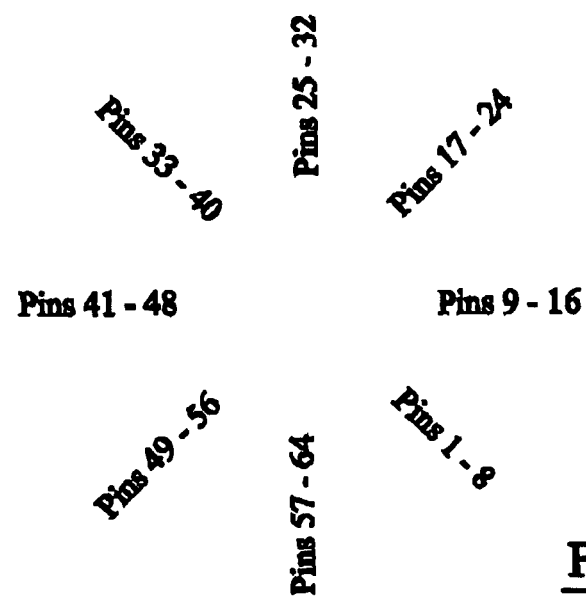
FIG. 1a illustrates the circumferential positioning of pins in a model and contacts on a test rig.

Whenever an electric current is passed through a location, an electric field is generated. The material, thickness of material, shape and configuration of the location all effect the size and shape of the electric field that results. Changes in one or more of these potential variables effect the electric field. In particular, corrosion of a location, such as a pipeline, generally reduces the thickness of material, increases the resistance and hence the voltage drop between different positions along the location in the direct of current flow.

The field effect method makes use of this basic principal to provide information on corrosion, erosion or other metal losses. The method applies an excitation current to the location under consideration for a short time period, fractions of a second, and measures the voltage drops between a large number of different pairs of electrical contacts touching the location. By considering the results the progress of corrosion can be evaluated. In general, the results are considered in terms of a fingerprint coefficient, Fc, for a given pair of electrical contacts with time. A reference pair of electrodes is provided on a non-corroding material through which the excitation current passes on its way to the location. This reference is generally employed so that variations, occurring between measurements, in a current provided by the power supply do not effect the measurements.

The temperature of the reference pair of electrodes and different pairs of electrical contacts touching the location is measured so as to correct for any variation in temperature between measurement times, and the effect of that temperature variation would have on the signals arising.

Information on general corrosion due to a general variation in the field over time can be investigated and monitored, and/or localised corrosion can be investigated and monitored where variations occur for only some of the pairs of electrical contacts.

Whilst the relationship between corrosion and observed electric field configuration changes and/or voltage variations between pairs of electrical contacts is fairly well known for linear configurations, such as straight pipes, the more complicated the configuration of the location, the less is known about this inter-relationship, particularly where non-even or localised wear/corrosion occurs. The latter situation is of course more common in non-linear configurations of locations being investigated, such as pipe bends, pipe junctions or more specific locations where non-even wear occurs, such as pits in surfaces etc.

In most practical cases it is not a viable option to verify or calibrate field signature based measurements using pre and post erosion measurements using other means or physical inspection. The benefits of field signature based analysis are lost in such cases.

As a consequence, there is a need to be able to relate measured voltages and electrical field configurations to the corrosion/erosion actually occurring within a location with a sufficient degree of accuracy to be confident in the link.

With a view to providing a technique for determining such a relationship, the present invention uses a technique based around a computer model of the location under investigation to obtain predicted values for the characteristics which link the actual measured signature to the actual corrosion arising in the real life location being investigated. As a first a example, a pipe bend is considered.

Figure 1B:
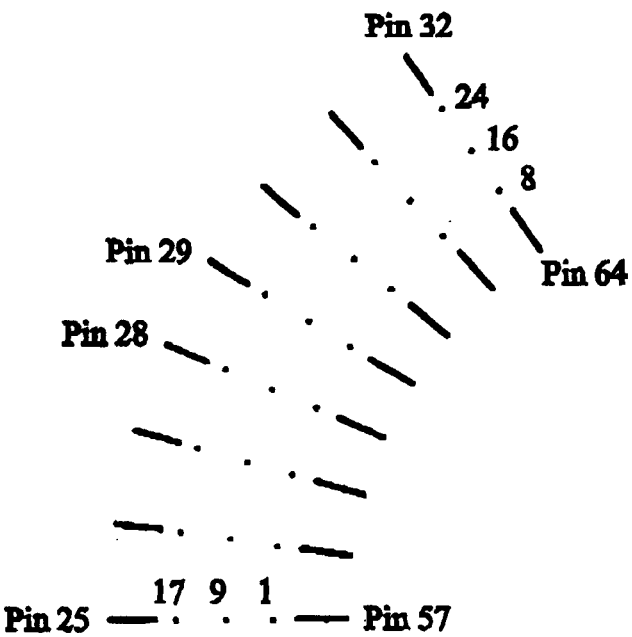
FIG. 1b illustrates the axial positioning of a series of pins in a model and contacts on a test rig for considering a pipe bend.

As shown in FIG. 1a, a series of electrical contacts in the form of pins are positioned along the length of the pipe at various positions around a circumference of the pipe length. Thus pins 25 to 32 are positioned along the top of the pipe length, whereas pins 57 to 64 are positioned along the bottom of the pipe length. This configuration is shown more clearly in FIG. 1b where the length of the pipe is viewed. The pins are provided at regular spacing, but irregular spacing could be used. This configuration of pins is used to obtain actual measurements of the voltage drops between pin pairs for the real life location being investigated.

Figure 2:
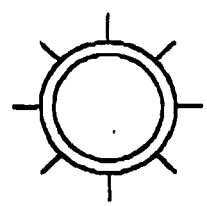
FIG. 2 illustrates the variation in wall thickness provided by the model.
Figure 2:
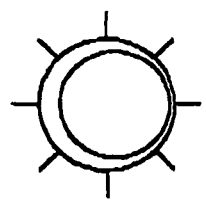
Figure 3:
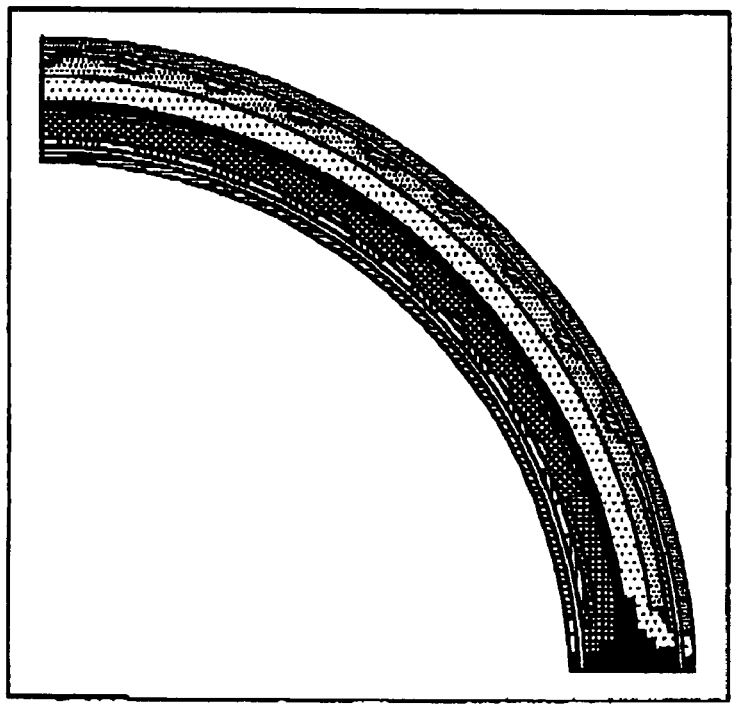
FIG. 3 illustrates the co-densities obtained for an un-eroded pipe according to the model.
Figure 4:
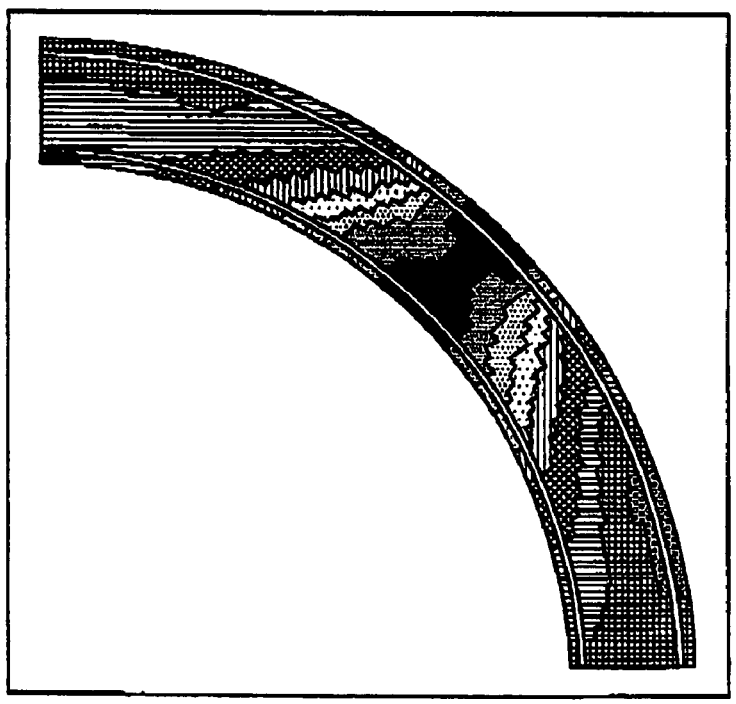
FIG. 4 illustrates the co-densities obtained for an eroded pipe according to the computer model, and having non-uniform erosion.

It is preferred that this configuration of pins is used to generate the positions of a series of nodes in the computer model which are equated to the pins and hence the voltage drop measurement locations. Using this configuration of nodes pins in a computer model, the effect of erosion on the field signature is considered. In the model it is assumed that the maximum loss will occur towards the mid-point of the outside of the bend, namely somewhere between pins 28 and 29 in FIG. 1a. The erosion is simulated in the model by increasing the internal pipe diameter from the left hand illustration of FIG. 2 to the configuration in the right hand illustration. Thus the diameter is increased, but the thickness on the inside of the bend is maintained; in effect the centre of the increasing diameter is moved from left to right as the diameter is increased.

The model basically generates a representation of the location to be investigated, takes into account the material or materials it is made of so as to account for their resistance, the thickness and/or cross sectional profile of the location throughout its extent, and potentially other factors effecting the electric field arising when a current is passed. Such a model can for instance be generated using the finite element analysis (FEA) package from ANSYS and in particular using the module EMAG (3-D version).

By passing a current through the location modelled and calculating the induced voltage at each node corresponding to a pin location, a model measurement of the electric field for the location in that configuration can be obtained. The model can then be varied, for instance to simulate loss of material from one or more parts of the location, and the process can then be repeated to obtain a model of the electrical field and consequently of the voltage differences for the relevant nodes.

The voltage difference found between adjacent nodes representing pins in the model with no defect gives the original voltage, and this is compared with the voltage as the defect grows to give the FC coefficient, into the computer model. By comparing the signal from all node pairs which correspond to pin pairs (for instance in the form of contour plots) the geometries of the defect in the model and on the actual location can be compared. In principal, the relationship between signal and metal loss can be derived for any node pair/pin pair, but in practice this generally only needs to be done for the region exhibiting maximum metal loss as that is the region of most concern on the location.

To enable the model to work successfully, the model needs to contain sufficient nodes (both nodes corresponding to pins and other nodes) to allow the geometry of the location being investigated to be described with sufficient accuracy to reflect the actual location. Additionally, the metal loss needs to be simulated or ideally mimicked with as great a degree of accuracy as possible. This could be achieved by a number of methods, and in particular by simulating metal loss by deleting nodes (other than those representing pins) and/or by moving the position of nodes (other than those representing pins).

Using this principal, a model for both the uneroded and eroded pipe was generated for a location configuration comprising a 90° bend radius of 90 mm with a pipe of outside diameter 30 mm and 3 mm wall thickness constructed in 11 segments. One end of the pipe was held at ground potential in the model, and the other end of the pipe was injected with a current of 20 amps. The wall thickness of segments 1 and 11 remain constant whist the wall thickness on the outside of the bend of segment 6, the mid-section, was reduced in a series of steps, 0.01, 0.02, 0.03, 0.05, 0.1, 0.15, 0.2, 0.3, 0.4, 0.6, 0.9, 1.2, 1.5, 1.8, 2.1 and 2.4 mm. Metal loss of intermediate segments was reduced proportionally.

Variations in current density arising obtained from considering the voltage drops from between the adjacent nodes/pins or the large series of nodes/pins can be used to give the fingerprint coefficient according to the formula:

$$Fc_x = \frac{v_{xn} - v_{xn+1}}{v_{0n} - v_{0n}} - 1 \times 1000 ppt$$

where $Fc_x$=fingerprint coefficient at x mm metal loss; $v_{xn}$ and $v_{xn+1}$ are the voltages at adjacent nodes/pins at x mm maximum metal loss; and $v_{0n}$ and $v_{0n+1}$ are the voltages at adjacent nodes/pins with no metal loss.

Figure 5:
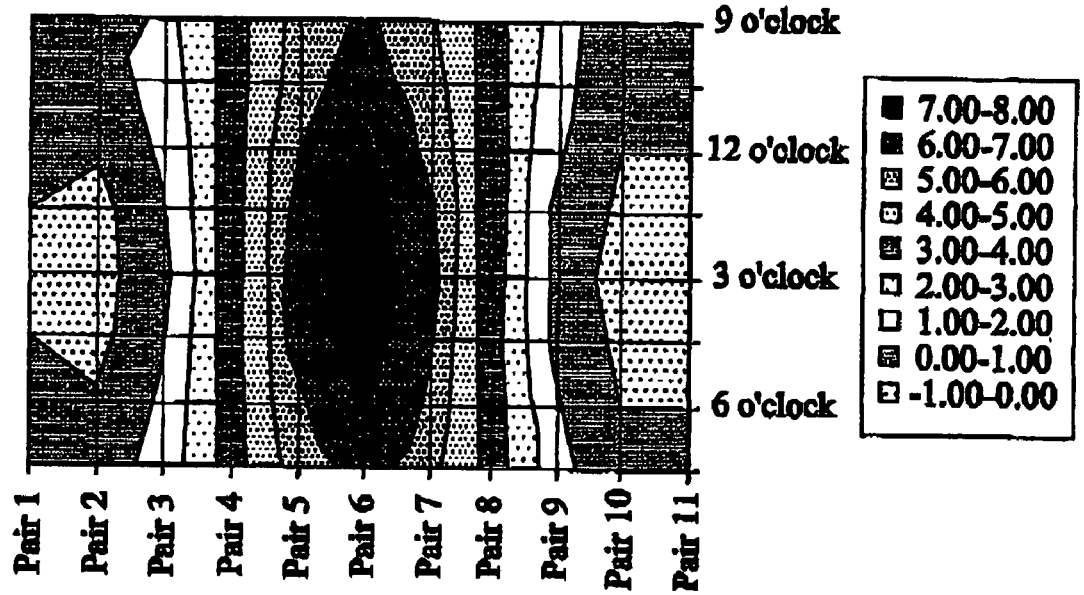
FIG. 5 illustrates in an unwrapped, plot, the Fc coefficients determined using a computer model for 50 microns maximum metal loss.
Figure 6:
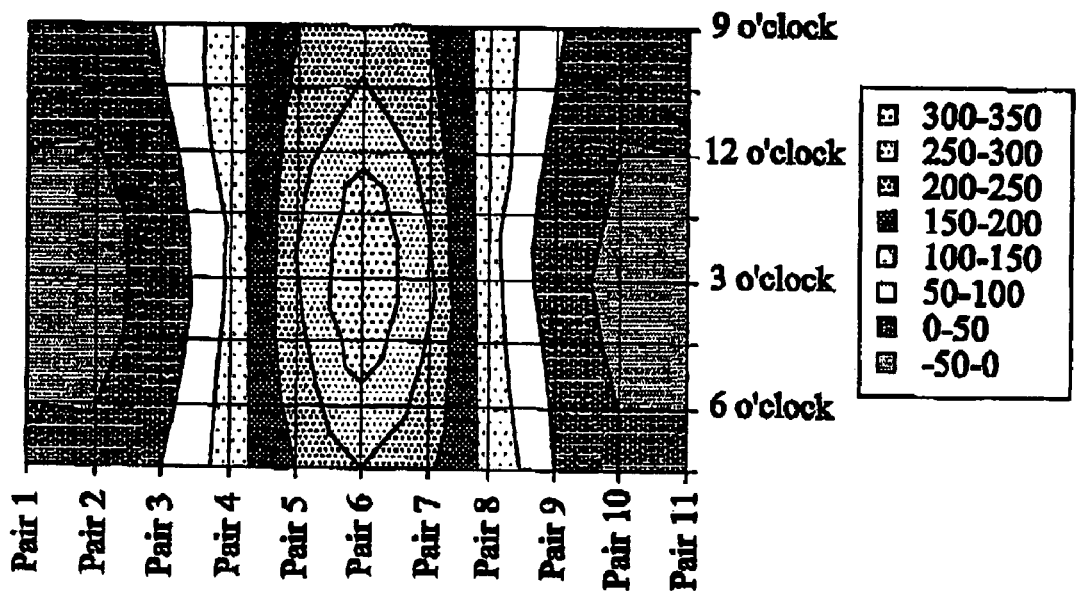
FIG. 6 illustrates in an unwrapped, plot, the Fc coefficients determined using a computer model for 1.5 mm maximum metal loss.

Fc coefficients derived according to this formula can be obtained for the various locations on the pipe. If the pipe is along its length at the 9 o'clock position, and the plot is flattened out, then the type of illustration represented by FIGS. 5 and 6 are obtained. FIG. 5 illustrates the position with 50 microns maximum metal loss being calculated, whereas FIG. 6 illustrates the position of 1.5 mm maximum metal loss. In each of these plots, whilst no metal loss occurred on the outside of the bend, the 9 o'clock position, an increase in the fingerprint coefficient was obtained. This is because the erosion represents an overall reduction in the cross sectional area of the pipe, and as a consequence an increase in the local current density.

Figure 7:
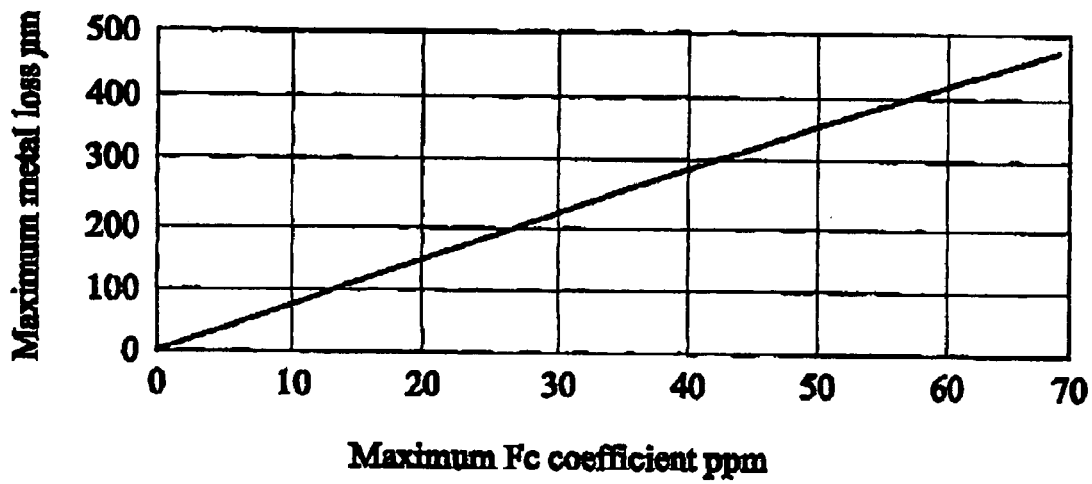
FIG. 7 illustrates the relationship between maximum Fc coefficient for the model and maximum metal loss.

The relationship between maximum metal loss which is a variable known in the model and the maximum Fc coefficient ppt which is determined from the results arising from the model can be represented graphically as shown in FIG. 7, and hence allows any maximum Fc coefficient to ppt to be related to the maximum metal loss in microns. This relationship is useful in considering actual test results for configurations of generally the same configurations of the model location.

Figure 8:
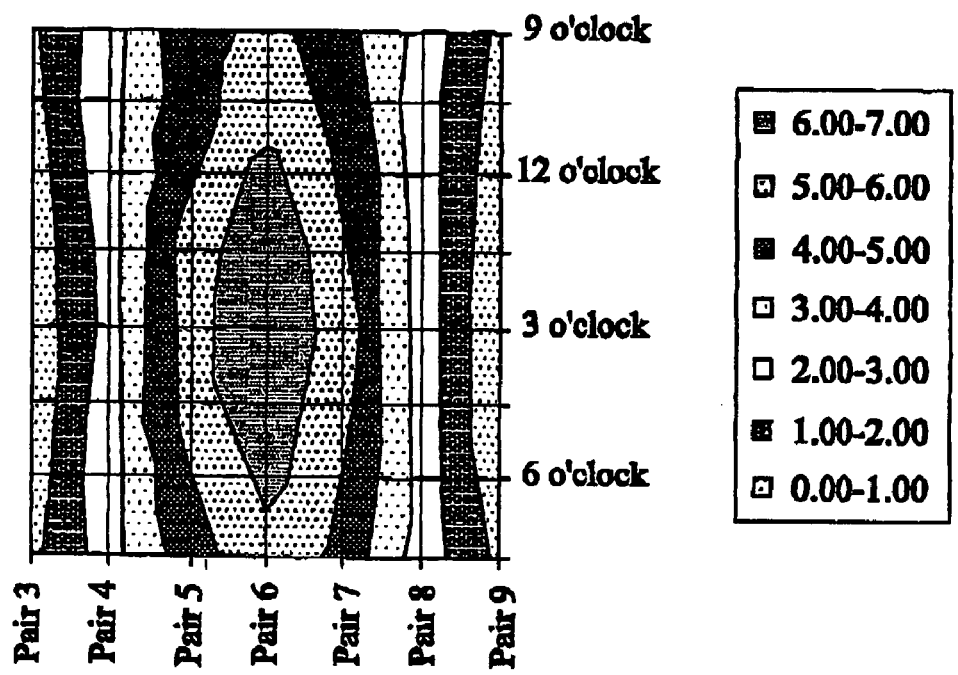
FIG. 8 illustrates in an unwrapped, plot, the Fc coefficients determined using a computer model for 16 micron maximum metal loss and with the offset effect on the Fc coefficients removed.
Figure 9:
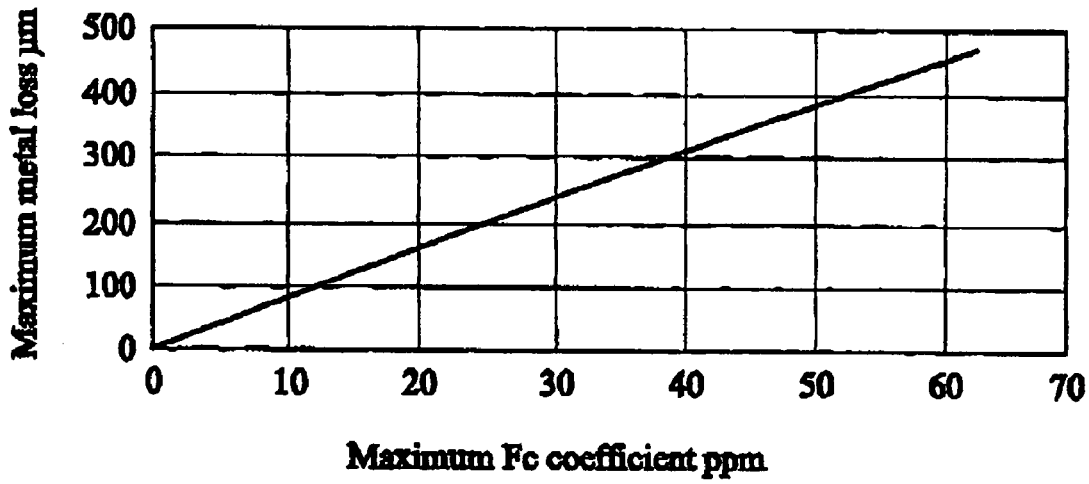
FIG. 9 illustrates the relationship between maximum Fc coefficient for the model and maximum metal loss with the offset removed.

The relationship can be more usefully refined, however, if an account for non-localised wear is made, and if variations in the applied current are accounted for. Removing these offsets results in the Fc coefficients displayed in FIG. 8, on this occasion for 60 micron maximum loss of wall thickness, and once again, the maximum metal loss and maximum Fc coefficient can be represented graphically against one another in this corrected form as shown in FIG. 9. In the case of FIG. 7 the maximum metal loss in microns equals $-0.0095Fc^2+7.42Fc$ whereas in the offset corrected formula of FIG. 9, the maximum metal loss in microns equals $-0.0013Fc^2+8.18Fc$.

Figure 10:
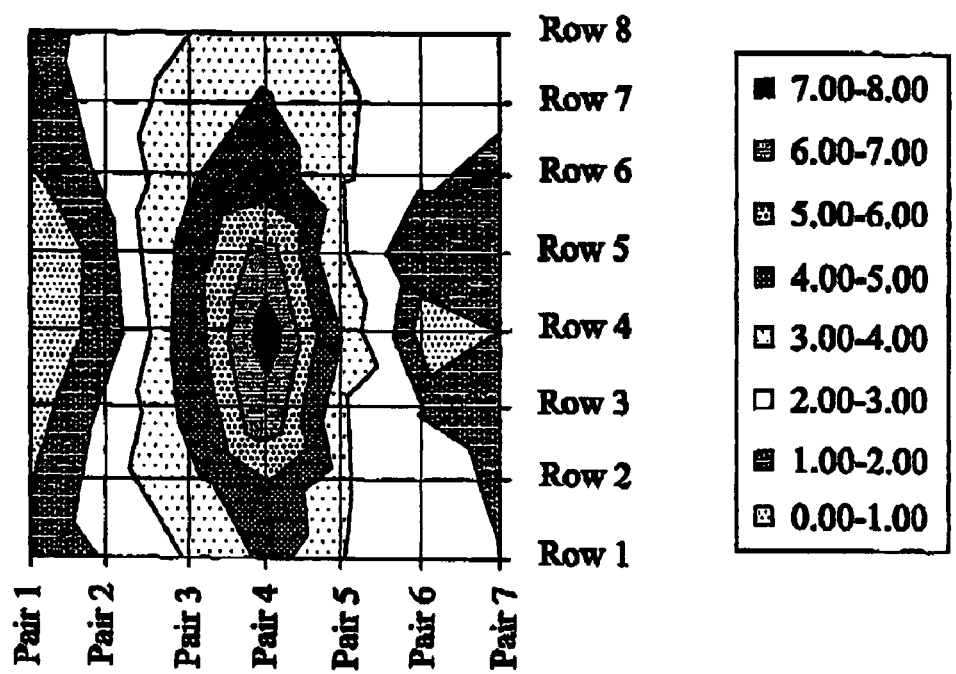
FIG. 10 illustrates the actual signals obtained from the test rig of corresponding configuration to the computer model.

To illustrate the applicability of this maximum metal loss determining function obtained from the model against real life situations, tests for matching model and test rig location configurations were undertaken. Test rig results are shown in FIG. 10 for one such test, and a comparison of FIG. 8 indicates that the model reasonably simulates the geometry of the localised defect.

Figure 11:
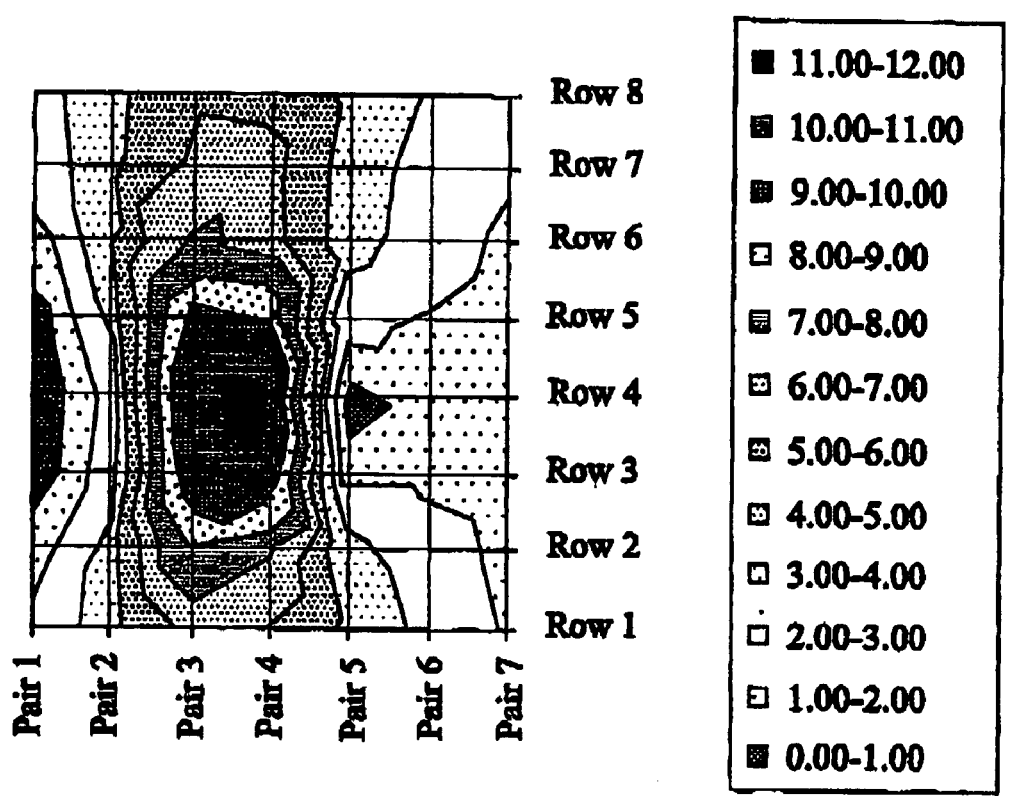
FIG. 11 illustrates the actual results obtained from a further test rig sample having a similar configuration to the computer model.

Results for an alternative test rig sample, presented in FIG. 11, again a reasonable comparison is obtained. The maximum Fx coefficient gives a localised metal loss of 90 microns, and this when added to a general erosion loss (estimated to be between 25 and 50 microns), gives a total metal loss of 150 to 145 microns as the prediction. Ultrasonic inspection of the actual test rig sample gave an erosion of 130 microns. Prediction of actual maximum metal loss occurring in real world vocations, therefore, based on characteristics obtained by modelling similar configurations gives an accuracy of measurement equivalent to ultrasonic investigation, but with better resolution as to the location of such localised corrosion.

Figure 12:
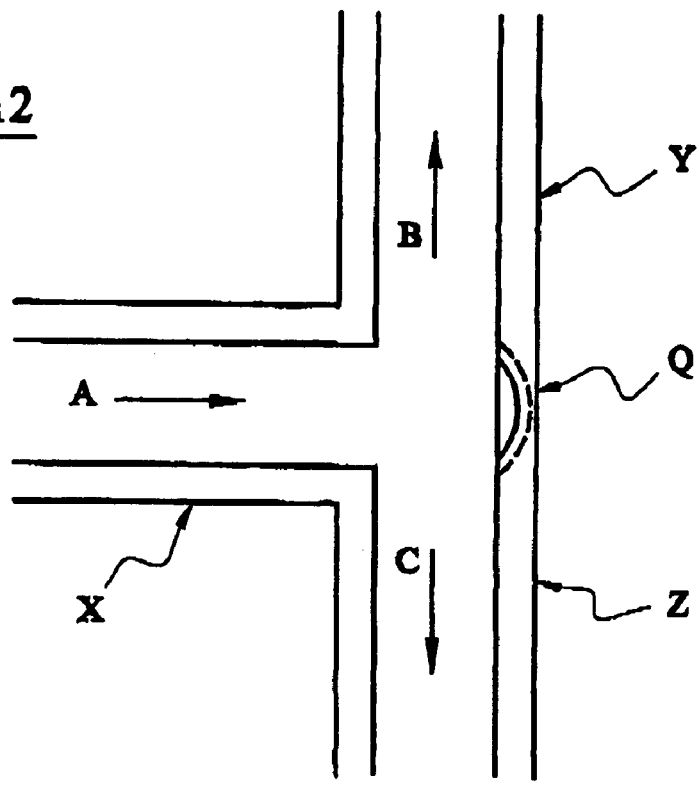
FIG. 12 illustrates an alternative location which is to be modelled.

Whilst the technique is exemplified above in relation to corrosion/erosion of the outside of a pipe bend, it is applicable to any situation where corrosion/erosion/metal loss can be simulated or mimicked using one or more models. For instance, it is possible to consider the real life location illustrated in FIG. 12 where flow along pipe X is indicated by arrow A, and splits at the junction to give flow in pipes Y and Z according to arrows B and C respectively. The impact of the flow on the outside of the junction at location Q may lead to dish style erosion/corrosion progressing. Again, this type of location can be modelled and the electric field and voltage drops modelled also with progressing corrosion simulated by reducing the material thickness throughout the general location Q, but with the reduction in metal thickness being greatest at the centre and of decreasing extent and separation away from that centre increases.

Figure 13A:
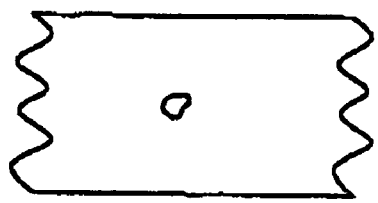
FIG. 13a to 13d illustrate a variety of different models of how metal loss is occurring which can be compared with actual results.
Figure 13B:
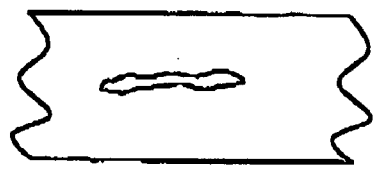
Figure 13C:
Figure 13D:
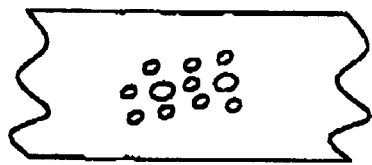

The technique is also applicable to considering locations where more localised and potentially less readily predictable corrosion/erosion/metal loss might occur. For instance as illustrated in FIG. 13, a part of an overall location, for instance a pipe, is illustrated in which quite localised corrosion/erosion/metal loss is occurring in the form of a pit over time. In FIG. 13a, the configuration of the pit shortly after its occurrence4 is illustrated. Pitting, however, may be less predictable than the type of material loss referred to above. However, it is possible to generate a variety of computer models of how the metal loss might occur with time to obtain model results relating to elongate pitting, FIG. 13b, as might occur along a seem or flaw; deep pitting, FIG. 13c, as might occur due to a localised but deep flaw and/or multiple small pitting, FIG. 13d, as might occur due to a more generalised issue with such a part of a location. In practice, the models results obtained from one or more of these scenarios can be compared with the results obtained from the actual real life location with time, with the most appropriate model being selected to quantify the metal loss occurring.

In general terms, the computer model can be used to enable the relationship between metal loss and Fc coefficient to be determined so long as the geometry of the metal loss that is occurring in practice can be satisfactorily duplicated in one or more models of the situation.

What is claimed is:

1. A method of investigating loss of material from a location, the method comprising:
   i) defining the actual location to be investigated;
   ii) providing two or more electrical contacts in contact with the actual location;
   iii) measuring the voltage between the two or more electrical contacts in contact with the location at a first time and at a second time, a current being passed through the location at the time of the voltage measurements, the voltage measurements having a relationship to the loss of material;
   iv) generating a model of the location configuration, the model including two or more points on that model of the location, modelling the values generated for the voltages which would be measured between the two or more points with a current applied to the model of the location at the first time;
   v) generating a further model of the location configuration at least at the second time, the further model including a change in location configuration between the first time and the second time to model loss of material from the location, the further model including two or more points on that further model of the location, modelling the values generated for the voltages which would be measured between the two or more points with a current applied to the further model of the location at the second time; and
   vi) comparing the model voltage differences with the voltage differences for the location at the second time, an alternative model of the location configuration being generated if the comparison is not acceptable, the model of the location configuration being equated to the location configuration if the comparison is acceptable;
   the differences between the location configuration of the first time and the acceptable comparison for the at least second time indicating the material loss from the actual location between the first and second times.

2. A method according to claim 1 in which the voltage differences are compared as fingerprint coefficients.

3. A method according to claim 2 which further comprises comparing the model voltage differences with the voltage differences for the location at the first time, an alternative model of the location configuration being generated if the comparison is not acceptable, the model of the location configuration being equated to the location configuration if the comparison is acceptable.

4. A method according to claim 1 which further comprises comparing the model voltage differences with the voltage differences for the location at the first time, an alternative model of the location configuration being generated if the comparison is not acceptable, the model of the location configuration being equated to the location configuration if the comparison is acceptable.

5. A method according to claim 1 in which the modelling process is a computer modelling process and the modelling process generates a three dimensional model of the location.

6. A method according to claim 5 in which the model includes a plurality of nodes, changes in the location configuration being simulated by deleting or moving nodes, the nodes deleted or moved not being nodes representing points at which voltage measurements are made.

7. A method according to claim 1 in which the modelling process includes information on the electrical resistance of the material and/or materials forming the location and/or configuration and/or cross sectional profile and/or thickness of the material or materials forming the location.

8. A method according to claim 1 in which a node is provided in the model for each pin in the actual measurement apparatus, the nodes have corresponding position and/or separation relative to the pins they represent.

9. A method according to claim 8 in which the modelling process includes applying a model electric current to the model location and calculating the induced voltage at two or more of the nodes, and ideally at all of the nodes, forming the model of the location.

10. A method according to claim 9 in which the modelling process includes the extraction of model voltages for the nodes corresponding to the pin positions in the actual apparatus and a calculation of voltage differences between node pairs.

11. A method according to claim 8 in which the modelling process includes the extraction of model voltages for the nodes corresponding to the pin positions in the actual apparatus and a calculation of voltage differences between node pairs.

12. A method according to claim 1 in which the modelling process includes calculating such voltages and/or voltage differences at the first time with no material loss, and at one or more other times with material loss.

13. A method according to claim 1 in which the change in the configuration of the model location involves a reduction in thickness of one or more parts of the location.

14. A method according to claim 1 in which the acceptability of the comparison is based on a statistical analysis and/or fitting process.

15. A method according to claim 1 in which the method includes the generation of a plurality of models based on different simulations of material loss and the consideration of which these models best represents the actual corrosion occurring.

16. A method according to claim 15 in which the model best representing the actual corrosion occurring is the one with correspondence of the model voltage differences and the actual location voltage differences.

17. A method according to claim 1 in which the relationship provides an expression of the corrosion as a thickness loss, proportion of material lost or a rate of loss.

18. A method according to claim 1 in which the factor relating to the model voltage values is a fingerprint coefficient and more particularly the maximum fingerprint coefficient measured for that configuration variation.

* * * * *